US010738605B2

(12) United States Patent
Stolle et al.

(10) Patent No.: US 10,738,605 B2
(45) Date of Patent: Aug. 11, 2020

(54) IN-SITU HIGH PRESSURE PH MEASUREMENT AND BIOFILM SAMPLING DEVICE (71) Applicants: Joseph W. Stolle, Wharton, TX (US); Yao Xiong, Houston, TX (US); Dennis R. Enning, Spring, TX (US); David S. Fischer, Houston, TX (US); Manuel A. Castelan, Pearland, TX (US)

(72) Inventors: Joseph W. Stolle, Wharton, TX (US); Yao Xiong, Houston, TX (US); Dennis R. Enning, Spring, TX (US); David S. Fischer, Houston, TX (US); Manuel A. Castelan, Pearland, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 229 days.

(21) Appl. No.: 15/915,202

(22) Filed: Mar. 8, 2018

(65) Prior Publication Data
US 2018/0275111 A1 Sep. 27, 2018

Related U.S. Application Data (60) Provisional application No. 62/477,135, filed on Mar. 27, 2017.

(51) Int. Cl.
E21B 49/08 (2006.01)
G01N 33/18 (2006.01)
G01N 33/28 (2006.01)

(52) U.S. Cl.
CPC ............ E21B 49/088 (2013.01); E21B 49/08 (2013.01); G01N 33/18 (2013.01); G01N 33/182 (2013.01); G01N 33/2847 (2013.01)

(58) Field of Classification Search
CPC .. G01N 33/18; G01N 33/182; G01N 33/2847; G01N 1/34; G01N 27/302; E21B 49/08–088
See application file for complete search history.

(56) References Cited

U.S. PATENT DOCUMENTS

| 8,245,572 | B2 | 8/2012 | Birkett et al. |
| 8,274,293 | B2 | 9/2012 | Sastry et al. |
| 2013/0025874 | A1* | 1/2013 | Saunders ................ E21B 49/08 166/357 |
| 2015/0122487 | A1 | 5/2015 | Lawrence et al. |

(Continued)

Primary Examiner — J. Christopher Ball
(74) Attorney, Agent, or Firm — ExxonMobile Upstream Research Company, Law Department (57) ABSTRACT A method for testing properties of a pressurized multiphase fluid sample containing at least hydrocarbons and water. The pressurized multiphase fluid sample is placed into a first pressurized chamber of a testing device. The water is separated from the hydrocarbons. At least part of the separated water is flowed through a first outlet in the first pressurized chamber and into a second pressurized chamber. The second pressurized chamber is optionally isolated from the first pressurized chamber. A pH level of the separated water is tested in the second pressurized chamber. Microbial activity and growth is tested for in the pressurized multiphase fluid in the first pressurized chamber. A pressure of the pressurized multiphase fluid is substantially maintained throughout the placing, separating, flowing, isolating, and testing steps.

13 Claims, 4 Drawing Sheets (56) References Cited

U.S. PATENT DOCUMENTS

2016/0003745 A1    1/2016   Lee et al.
2017/0030508 A1*   2/2017   Pilloni ................... C12Q 1/689
2017/0212272 A1*   7/2017   Monteiro ............... G01N 21/77

* cited by examiner

FIG. 6

IN-SITU HIGH PRESSURE PH MEASUREMENT AND BIOFILM SAMPLING DEVICE

CROSS REFERENCE TO RELATED APPLICATION

This application claims the benefit of U.S. Provisional Application Ser. No. 62/477,135, filed Mar. 27, 2017, the disclosure of which is incorporated herein by reference in its entirety.

FIELD OF THE INVENTION

The invention relates to corrosion mitigation in a flowline or pipeline, and more specifically, to a device for measuring and/or sampling corrosion-inducing conditions or agents in a flowline or pipeline fluid.

BACKGROUND

The fluid pH inside a flowline or pipeline is an important parameter for determining the corrosion mechanism in the flowline or pipeline and applying mitigation methods. Fluid pH further influences the partitioning of oilfield chemicals, so that a good understanding of fluid pH is important for oilfield chemical management. One common industry approach to determine pH is to conduct water chemistry analysis on the depressurized water sample and then back calculate the original pH based on the levels of bicarbonate, acetic acid/acetate, carbon dioxide ($CO_2$) and hydrogen sulfide ($H_2S$). However, the accuracy of this type of calculation is often limited by the accuracy of water chemistry analysis, especially the ratio between acetic acid and acetate. Currently there is no analytical technique able to distinguish acetic acid from acetate during the water chemistry analysis. Furthermore, certain species in the water sample, such as acetic acid and bicarbonate, are subject to change during the sampling and shipping process even before the analysis. Because of all those uncertainties, the pH prediction for a production unit can vary significantly between samples, hindering the determination of the corrosion mechanism in the sample, as well as potential corrosion mitigation methods. What is needed is a method for accurately measuring pH in a flowline or pipeline.

The formation of biofilms is another factor in flowline or pipeline corrosion. Biofilms are accumulations of microorganisms along with organic and inorganic deposits on surfaces. Biofilms form through the attachment and growth of planktonic (free-floating) microorganisms that are present in all aqueous environments, including water extracted from a hydrocarbon well. It has been discovered that certain biofilms that form on the interior surfaces of flowlines, pipelines, and pressure vessels can, when left uncontrolled, cause significant corrosion to the metal substrate. Such corrosion is referred to as microbiologically influenced corrosion (MIC). It is hence important to be able to collect, quantify and characterize such oilfield biofilms as part of a robust facility integrity program. Collection and analysis of biofilms helps determining the type and degree of MIC expected within a particular production environment. The most common point of access to biofilm for diagnosis and monitoring of MIC are corrosion coupons. However, many facilities lack corrosion coupons or cannot install corrosion coupons at locations of water drop out, which is where formation of corrosive biofilm is possible. What is needed is a method of testing corrosion coupons in an environment that maximizes their effectiveness.

SUMMARY OF THE INVENTION

The invention provides a method for testing properties of a pressurized multiphase fluid sample containing at least hydrocarbons and water. The pressurized multiphase fluid sample is placed into a first pressurized chamber of a testing device. The water is separated from the hydrocarbons. At least part of the separated water is flowed through a first outlet in the first pressurized chamber and into a second pressurized chamber. The second pressurized chamber is isolated from the first pressurized chamber. A pH level of the separated water is tested in the second pressurized chamber. Microbial activity and growth is tested for in the pressurized multiphase fluid in the first pressurized chamber. A pressure of the pressurized multiphase fluid is maintained throughout the placing, separating, flowing, isolating, and testing steps.

The invention also provides an apparatus for testing properties of a pressurized multiphase fluid sample containing at least hydrocarbons and water. The apparatus includes a first pressurized chamber into which the pressurized multiphase fluid sample and one or more corrosion coupons are placed. A second pressurized chamber is connected to the first pressurized chamber through a first outlet. A first valve is disposed between the first pressurized chamber and the second pressurized chamber. The first valve opens to permit water separated out of the pressurized multiphase fluid sample in the first pressurized chamber to flow into the second pressurized chamber. The first valve closes to prevent hydrocarbons in the pressurized multiphase fluid sample from flowing into the second pressurized chamber from the first pressurized chamber. A pH probe is positioned to test a pH level of the separated water in the second pressurized chamber. A viewing port is disposed in the first pressurized chamber to permit visual inspection of at least one of the pressurized multiphase fluid sample and the one or more corrosion coupons in the first pressurized chamber.

The invention also provides a method for testing properties of a pressurized multiphase fluid sample containing at least hydrocarbons and water. The pressurized multiphase fluid sample is placed into a first pressurized chamber of a testing device. The water is separated from the hydrocarbons. At least part of the separated water is flowed through a first outlet in the first pressurized chamber and into a second pressurized chamber. The second pressurized chamber is isolated from the first pressurized chamber. A pH level of the separated water is tested in the second pressurized chamber. A pressure of the pressurized multiphase fluid is maintained throughout the placing, separating, flowing, isolating, and testing steps.

DETAILED DESCRIPTION

Various specific aspects and versions of the present disclosure will now be described, including preferred aspects and definitions that are adopted herein. While the following detailed description gives specific preferred aspects, those skilled in the art will appreciate that these aspects are exemplary only, and that the present invention can be practiced in other ways. Any reference to the "invention" may refer to one or more, but not necessarily all, of the aspects defined by the claims. The use of headings is for purposes of convenience only and does not limit the scope of the disclosed aspects. For purposes of clarity and brevity, similar reference numbers in the several Figures represent similar items, steps, or structures and may not be described in detail in every Figure.

All numerical values within the detailed description and the claims herein are modified by "about" or "approximately" the indicated value, and take into account experimental error and variations that would be expected by a person having ordinary skill in the art.

"Exemplary" is used exclusively herein to mean "serving as an example, instance, or illustration." Any embodiment described herein as "exemplary" is not to be construed as preferred or advantageous over other embodiments.

A "mixed phase fluid" as used herein is a fluid containing constituents at two or more phases of matter. For example, a liquid-solid mixed phase fluid contains liquid matter and solid particulate matter flowing within the liquid. Two immiscible liquids may form so called liquid-liquid mixed phase fluids. A gas and liquid dispersion is a gas-liquid mixed phase fluid containing a liquid and dispersed gas bubbles within the flowable fluid mixture.

A "facility" as used herein is a representation of a tangible piece of physical equipment through which hydrocarbon fluids are either produced from a reservoir or injected into a reservoir. In its broadest sense, the term facility is applied to any equipment that may be present along the flow path between a reservoir and the destination for a hydrocarbon product. Facilities may include production wells, injection wells, well tubulars, wellhead equipment, gathering lines, manifolds, pumps, compressors, separators, surface flow lines and delivery outlets. In some instances, the term "surface facility" is used to distinguish those facilities other than wells. A "facility network" is the complete collection of facilities that are present in the model, which would include all wells and the surface facilities between the wellheads and the delivery outlets.

The term "gas" is used interchangeably with "vapor," and means a substance or mixture of substances in the gaseous state as distinguished from the liquid or solid state. Likewise, the term "liquid" means a substance or mixture of substances in the liquid state as distinguished from the gas or solid state. As used herein, "fluid" is a generic term that may include either a gas or vapor.

A "hydrocarbon" is an organic compound that primarily includes the elements hydrogen and carbon although nitrogen, sulfur, oxygen, metals, or any number of other elements may be present in small amounts. As used herein, hydrocarbons generally refer to organic materials that are transported by pipeline, such as any form of natural gas or oil. A "hydrocarbon stream" is a stream enriched in hydrocarbons by the removal of other materials such as water and/or any additive.

"Pressure" is the force exerted per unit area by the gas on the walls of the volume. Pressure can be shown as pounds per square inch (psi). "Atmospheric pressure" refers to the local pressure of the air. "Absolute pressure" (psia) refers to the sum of the atmospheric pressure (14.7 psia at standard conditions) plus the gauge pressure (psig). "Gauge pressure" (psig) refers to the pressure measured by a gauge, which indicates only the pressure exceeding the local atmospheric pressure (i.e., a gauge pressure of 0 psig corresponds to an absolute pressure of 14.7 psia). The term "vapor pressure" has the usual thermodynamic meaning. For a pure component in an enclosed system at a given pressure, the component vapor pressure is essentially equal to the total pressure in the system.

"Production fluid" refers to a liquid and/or gaseous stream removed from a subsurface formation, such as an organic-rich rock formation. Produced fluids may include both hydrocarbon fluids and non-hydrocarbon fluids. For example, production fluids may include, but are not limited to, oil, natural gas and water.

"Substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

Certain aspects and features have been described using a set of numerical upper limits and a set of numerical lower limits. It should be appreciated that ranges from any lower limit to any upper limit are contemplated unless otherwise indicated. All numerical values are "about" or "approximately" the indicated value, and take into account experimental error and variations that would be expected by a person having ordinary skill in the art.

All patents, test procedures, and other documents cited in this application are fully incorporated by reference to the extent such disclosure is not inconsistent with this application and for all jurisdictions in which such incorporation is permitted.

Described herein are methods and processes to in-situ high pressure pH measurement device. According to disclosed aspects, one can directly measure the pH of a pressurized fluid sample from a pipeline or other source of pressurized multiphase fluid, without depressurization or losing any chemical species. The disclosed apparatus and method is intrinsically safe and can be installed in a production field. Operators can use the disclosed device to either periodically check or continuously monitor the fluid pH, without additional sampling or analysis. The disclosed device can support the evaluation of corrosion susceptibility in the field, and can further assist in determining the correct corrosion mitigation methodology. In addition to in-situ, high pressure pH measurement, the disclosed apparatus and method can collect biofilm developed on metal surfaces. Corrosion coupons, made of pipeline steel (and electrically isolated from the sample collection chamber), are placed in the sample collection chamber for growing biofilm. Specific aspects of the disclosure include those set forth in the following paragraphs as described with reference to the Figures. While some features are described with particular reference to only one Figure, they may be equally applicable to the other Figures and may be used in combination with the other Figures or the foregoing discussion.

Figure 1:
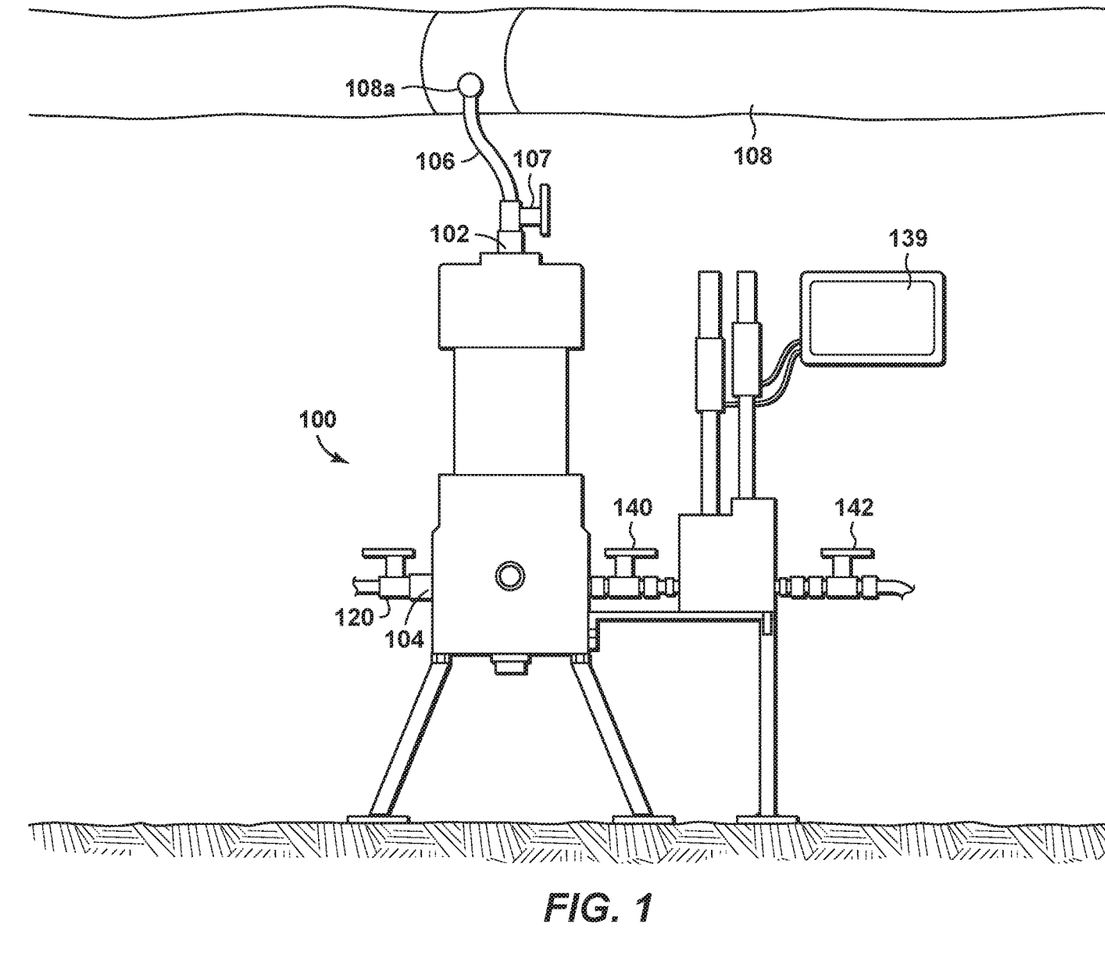
FIG. 1 is a side elevational view of a measuring and testing device according to disclosed aspects.

FIG. 1 depicts an in-situ sampling device 100 according to aspects of the disclosure. Device 100 has a fluid inlet 102 and a fluid outlet 104. A length of pipe and/or tubing 106 may selectively connect the fluid inlet 102 to a pipeline, flowline, separator, storage tank, vessel, or other pressurized source of a pressurized multiphase fluid to be monitored and/or tested. By way of non-limiting example, a pipeline 108 carrying a pressurized multiphase production fluid is shown in the figures and discussed further herein, it being understood that other pressurized fluids and fluid sources are contemplated and encompassed by the following description. A fluid inlet valve 107 may connect tubing 106 to fluid inlet 102. The device 100 may comprise a stand-alone unit as shown in the Figures, in which case the device is supported on one or more legs 109. As depicted in more detail in FIG. 2, the fluid inlet may be formed in a top lid 110, which is secured to a first end of an extension tube 112. The extension tube can be sized or replaced with a differently sized extension tube to modify the maximum volume of the primary pressurized chamber, depending on the level of water cut in the production fluid. The second end of the extension tube 112 is secured to a primary base 114, in which a primary pressurized chamber 116 is formed. The primary pressurized chamber may be an open or hollowed-out section of the primary base 114. The fluid outlet 104 permits fluid to flow out of the primary pressurized chamber 116. A fluid outlet valve 120 may be positioned at fluid outlet 104 to selectively control the passage of fluid through the fluid outlet. A sampling outlet 122 directs fluid to a secondary pressurized chamber 124. A viewing port 126 may be installed in the primary base 114 so that the interior of the primary pressurized chamber 116 may be viewed by an operator or observer. Preferably the location of the viewing port 126 is at the same vertical position as the sampling outlet 122 so that the operator can see which fluid phase (water, oil, gas, or an emulsion) is present at that level. According to the aspects of the disclosure depicted in FIG. 2, the viewing port is located near the bottom of the primary pressurized chamber 116. The viewing port may be made of glass, plastic, or any other material capable of withstanding the pressure in the primary pressurized chamber 116 while being sufficiently transparent or translucent to permit the operator to observe the fluid level and phase inside the primary pressurized chamber. An additional viewing port may be used to view the production fluid or to illuminate the interior of the primary pressurized chamber 116 using an exterior light source (not shown).

Figure 2:
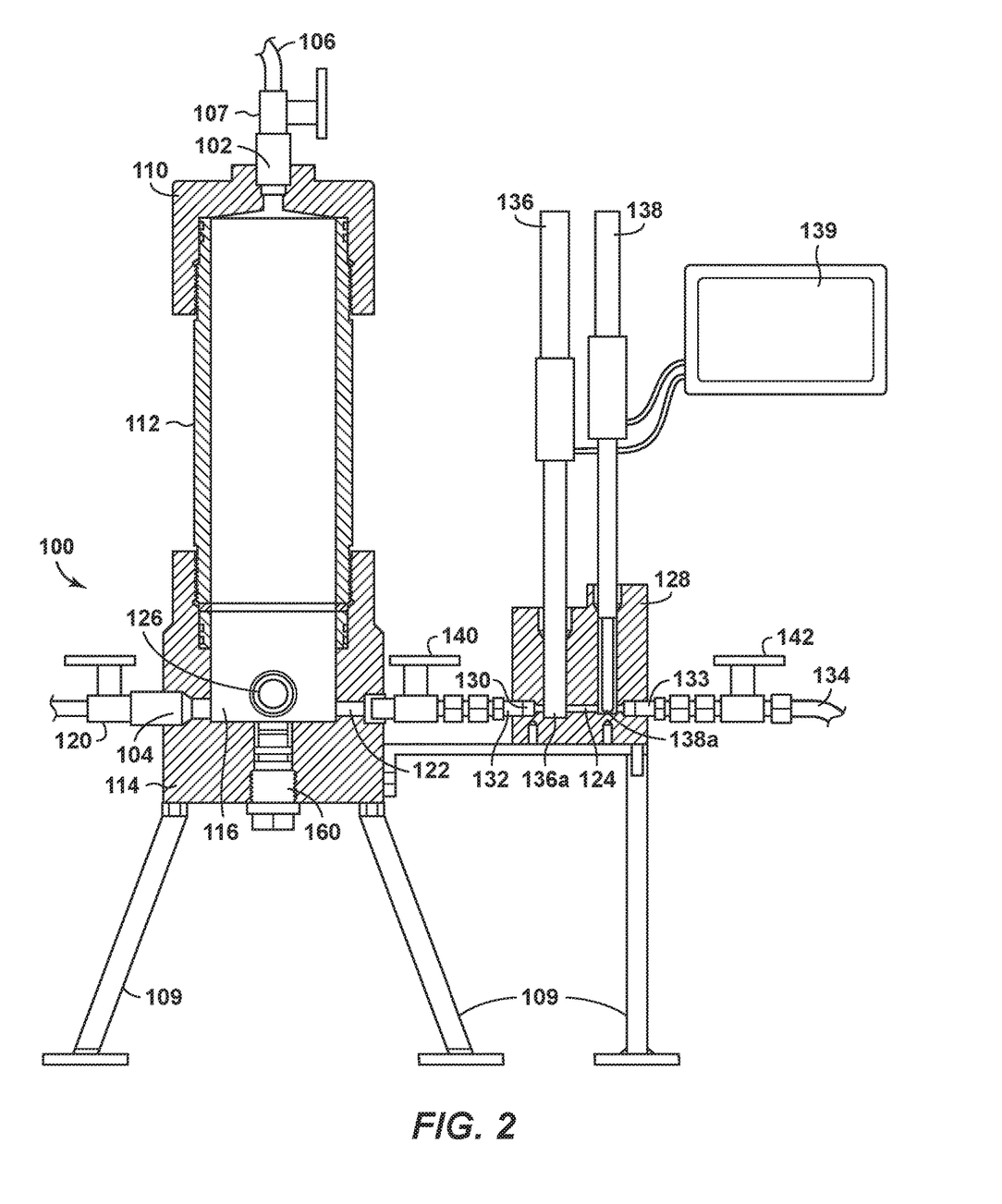
FIG. 2 is a cutaway view of the measuring and testing device shown in FIG. 1.

The secondary pressurized chamber 124 may be formed in a secondary base 128, which may or may not be integrally formed with the primary base 114. The secondary pressurized chamber 124 is shown connected to a fluid passageway 130 having an inlet 132 in fluid communication with the primary pressurized chamber 116. The fluid passageway 130 is also in fluid communication with an outlet 133, which in turn is connected through tubing or piping 134 to a wastewater bucket or slurry tank (not shown). The secondary pressurized chamber 124 also includes one or more testing probes. As shown in FIG. 2, the testing probes may include a high pressure pH probe 136 capable of measuring the pH level of fluid in the secondary pressurized chamber. The testing probes may also include a high pressure reference probe 138, which may be a silver/silver chloride (Ag/AgCl) probe. The testing probes may be temporarily or permanently attached to a dual port pH meter 139 that communicates a pH measurement to an operator. The secondary pressurized chamber 124 may be selectively isolated using first and second valves 140, 142. All components of device 100 are designed and selected to withstand normal operating pressures of the production fluid over a significant period of time, which in some cases may be as high as 1,500 psia. Desirably, the system is designed to hold pressures for a significant amount of time (e.g., at least a day, a week or a month) without a substantial loss of pressure.

To operate the device 100, all valves and ports are properly positioned and checked for leaks. The pH probe may be calibrated before each use, preferably using calibration solutions of pH 4 and 7. Production fluid taken from a sampling port 108a in pipeline 108 is then flowed through primary pressurized chamber 116. This is accomplished by opening fluid inlet valve 107 and fluid outlet valve 120. The production fluid passes through tubing 106 and into fluid inlet 102. The production fluid, which typically includes multiple phases such as gas, water, and oil, will then flow into the extension tube 112 and the primary pressurized chamber 116. When it is determined that an acceptable flow sample can be obtained from the production fluid flowing through primary pressurized chamber 116, fluid outlet valve 120 is closed. Fluid inlet valve 107 is left open to allow the pressure inside the primary pressurized chamber has attained a desired amount. As the primary pressurized chamber is at this point in fluid communication with fluid in pipeline 108, the pressure in the pressurized chamber may increase to be equal to, substantially equal to, or to approximate the pressure of the fluid in the pipeline. Fluid outlet valve 120 is then closed. This process of obtaining a fluid sample (i.e., flowing fluid through the primary pressurized chamber and placing a fluid sample under pipeline pressure) may be repeated by opening and closing the fluid outlet valve 120 while maintaining fluid inlet valve 107 in an open position. When a desired fluid sample has been obtained at a desired pressure level, the fluid inlet valve 107 may remain open (to maintain pressure in the device) or optionally be closed and fluid outlet valve 120 is closed. The fluid sample is maintained in the extension tube and primary pressurized chamber until the oil and water in the fluid sample have separated. If oil and water form an emulsion inside the chamber, it will take time (from several minutes to several days) for the oil and water to separate. An operator or observer, looking through the viewing port 126, can determine whether water is separated out from the oil or emulsion. Once the water is separated out in the primary pressurized chamber, the first valve 140 is opened, allowing the separated water to flow into the secondary pressurized chamber. Second valve 142 is opened slightly to flush out the secondary pressurized chamber 124, thereby purging the secondary pressurized chamber of any oil contained therein. During the flushing step, it is normally desired to maintain the fluid inlet valve 107 may remain open to maintain pressure in the system at the pressure of the pipeline 108. Opening the second valve 142 also permits the separated water to flow into the secondary pressurized chamber. The respective tips 136a, 138a of the pH probe 136 and reference probe 138 are located in the path of fluid flow, and therefore an immediate pH reading will be obtained once the tips 136a, 138a are in contact with the separated water.

The presence of a significant amount of oil in the secondary pressurized chamber may compromise the pH reading by the pH probe 136 and/or the reference probe 138. Therefore, to ensure the fluid flowing into the secondary pressurized chamber is mostly the separated water, the second valve 142 may be opened slowly to check the fluid flowing out of the fluid outlet 104. If the fluid appears to be substantially all water, the second valve 142 may be closed. The pH value of the fluid will be shown on the pH meter immediately but it may take one or two minutes to reach a stable reading. Small amounts of oil droplets or emulsion present in the separated water flowing out of the outlet 133 when the second valve 142 is opened should not affect the pH reading. However, a large quantity of oil or emulsion in the secondary pressurized chamber 124 may invalidate the pH reading as the probes can be contaminated by the oil/emulsion. Such contaminated probes will need to be removed from the device 100 and cleaned.

Figure 3:
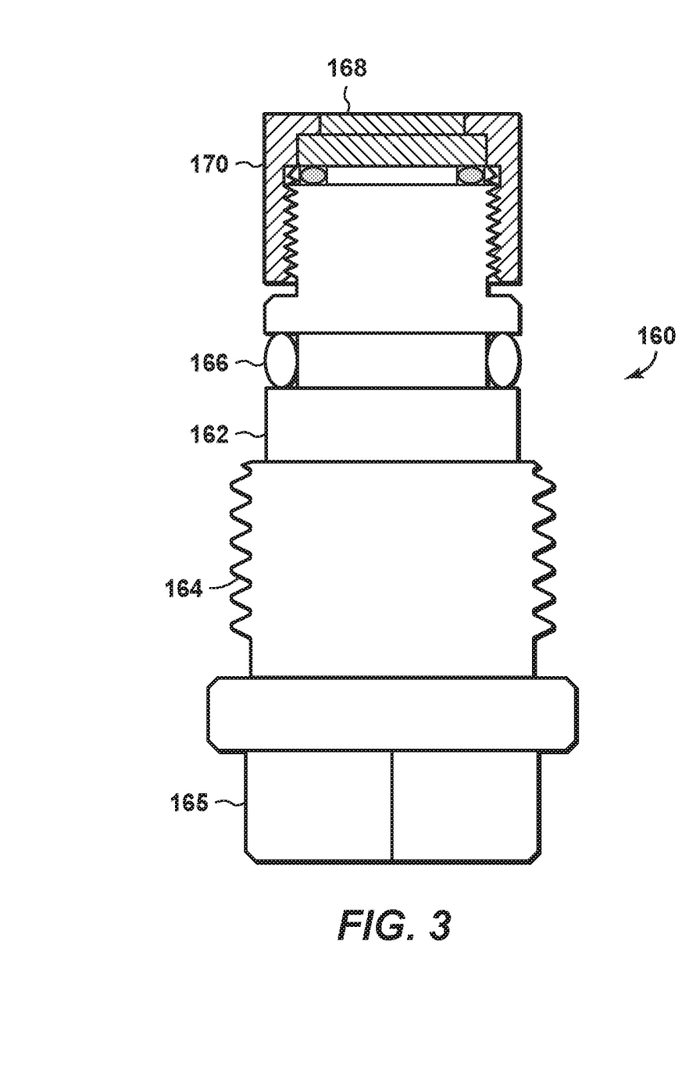
FIG. 3 is a side elevational view of a coupon holder according to disclosed aspects.
Figure 4:
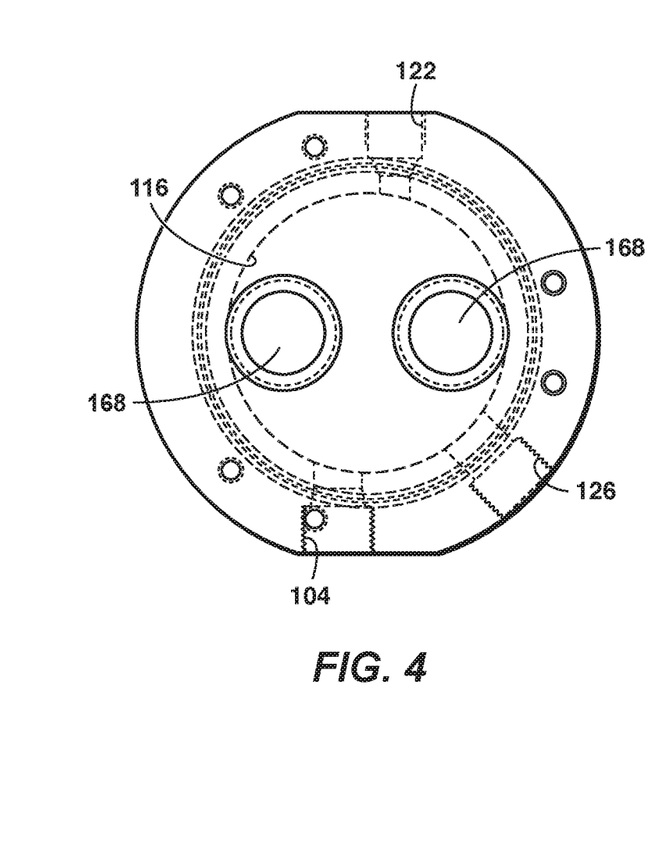
FIG. 4 is a top plan view of the interior of a pressurized chamber of the measuring and testing device shown in FIGS. 1 and 2.

In addition to measuring the pH of a production fluid, device 100 may be used to collect and/or grow biofilms developed on removable carbon steel (or other types of steel) corrosion coupons. The coupons may be exposed to production fluid in the primary pressurized chamber for sufficient time for the biofilms to grow. As shown in FIG. 2, one or more coupon holders 160 are configured to be screwed, inserted, or otherwise placed in the primary base 114. A more detailed view of coupon holder 160 according to disclosed aspects is provided in FIG. 3. The coupon holder includes a body portion 162, which may include threads 164 and a tooled head 165 shaped to be contacted by a wrench or other tool. In this manner the coupon holder 160 may be screwed into the primary base 114 and in communication with the primary pressure chamber 116. An optional O-ring 166 prevents production fluid from leaking past the body portion 162. The corrosion coupon 168 is placed at an end of the coupon holder. A threaded cap 170 holds the corrosion coupon 168 in place. FIG. 4 is a top plan view of the interior of primary pressurized chamber 116 and shows how the one or more corrosion coupons 168, fastened to the top of a respective coupon holder 160, are positioned inside the primary pressurized chamber 116. The one or more corrosion coupons thereby provide a waterwet metal surface for oilfield microorganisms in a production fluid to grow under field-like conditions (including pressure). The one or more corrosion coupons 168 are preferably secured in the primary pressurized chamber in such a manner to be electrically isolated from the remainder of the primary pressurized chamber. In operation, the production fluid is permitted to flow into the primary pressurized chamber 116 and then the primary pressurized chamber 116 is isolated. The water and oil components of the production fluid are permitted to separate, and the water can be permitted to exit the primary pressurized chamber through the fluid outlet 104 or through secondary outlet 122. Additionally, the water component of the production fluid can contact the one or more corrosion coupons 168 to permit biofilm growth to occur thereon. During the biofilm growth period, the primary pressurized chamber 116 may be periodically flushed with fresh production fluid to provide sufficient nutrients for sustaining microbial activity and growth on the water-wet corrosion coupons. This may be done by causing fluid in the primary pressurized chamber 116 to exit through the fluid outlet 104 and causing fresh production fluid to enter the primary pressurized chamber through the fluid inlet 102. It is possible by the proper orientation of viewing port 126 to visually observe the surface conditions of the corrosion coupons through the viewing port 126. Additional viewing ports may be needed to adequately view the coupons. After establishing sufficient amounts of biofilm on the surface of the corrosion coupons 168, which may take up to two weeks, or up to four weeks, or up to six weeks or up to ten weeks, or up to six months, the primary pressurized chamber 116 is drained through the fluid outlet 104 by opening the fluid outlet valve 120. The corrosion coupons may then be removed by unscrewing the coupon holder 160 from the primary base 114. The biofilm samples on the corrosion coupons may then undergo biological analysis, which may include DNA-based techniques, adenosine triphosphate (ATP) assays, or other techniques commonly used in petroleum microbiology. Furthermore, any inorganic corrosion products formed on the one or more coupons may be chemically analyzed and characterized. Overall, the analysis of these biofilms may provide access to the data needed to understand the possible contribution of microorganisms to corrosion in a particular pipeline.

Figure 5:
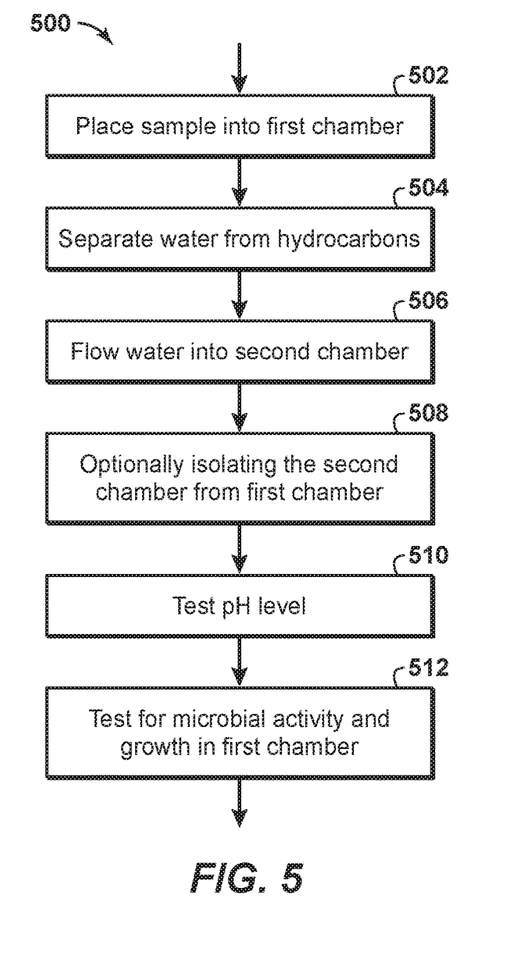
FIG. 5 is a flowchart showing a method according to disclosed aspects.

FIG. 5 is a method 500 for testing properties of a pressurized multiphase fluid sample containing at least hydrocarbons and water. At block 502 the pressurized multiphase fluid sample is placed into a first pressurized chamber of a testing device. At block 504 the water is separated from the hydrocarbons. At block 506 at least part of the separated water is flowed through a first outlet in the first pressurized chamber and into a second pressurized chamber. At block 508 the second pressurized chamber is optionally isolated from the first pressurized chamber. At block 510 a pH level of the separated water is tested in the second pressurized chamber. At block 512 microbial activity and growth is tested for in the pressurized multiphase fluid in the first pressurized chamber. In preferred embodiments, it is desired that a pressure of the pressurized multiphase fluid is maintained throughout the placing, separating, flowing, isolating, and testing steps. This pressure should be substantially the same (e.g., within 5%+/−, 10%+/−, or 20%+/−) of the pressure of the pipeline 108 from which the sample was obtained.

Figure 6:
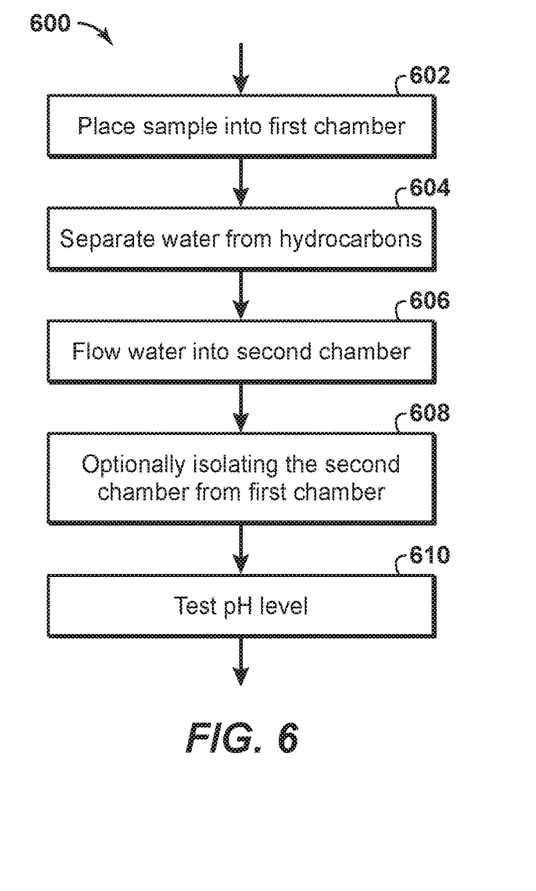
FIG. 6 is a flowchart showing a method according to disclosed aspects.

FIG. 6 is a method 600 for testing properties of a pressurized multiphase fluid sample containing at least hydrocarbons and water. At block 602 the pressurized multiphase fluid sample is placed into a first pressurized chamber of a testing device. At block 604 the water is separated from the hydrocarbons. At block 606 at least part of the separated water is flowed through a first outlet in the first pressurized chamber and into a second pressurized chamber. At block 608 the second pressurized chamber is optionally isolated from the first pressurized chamber. At block 610 a pH level of the separated water is tested in the second pressurized chamber. In preferred embodiments, it is desired that a pressure of the pressurized multiphase fluid is maintained throughout the placing, separating, flowing, isolating, and testing steps. This pressure should be substantially the same (e.g., within 5%+/−, 10%+/−, or 20%+/−) of the pressure of the pipeline 108 from which the sample was obtained.

Aspects of the disclosure may be modified in many ways while keeping with the spirit of the invention. The dual port pH meter 139, shown as being removable from device 100, may instead be permanently attached to the device. In addition, the various separately described components may be combined into single components; for example, top lid 110 and extension tube 112 may be integrally formed or even welded together. Additionally, the extension tube 112 and the primary base 114 may be integrally formed.

The aspects disclosed herein provide a method and apparatus for in-situ testing of production fluid at operating pressures. An advantage of the disclosed aspects is the portability and installation flexibility of the disclosed device. Instead of configuring the device as a freestanding apparatus, the disclosed device may be attached to other equipment or to a skid holding other equipment, or may be attached directly on a flowline or pipeline or other fluid receptacle. The disclosed device is non-intrusive to the pipeline and therefore has no impact on hydrocarbon production. The disclosed device has been found to be intrinsically safe for use in typical oil and gas production fields. The disclosed device also has been found to resist at least 1,500 psia total pressure and provide stable pH readings for extended periods of time.

Another advantage is that the disclosed device can provide a technical solution to grow and access oilfield biofilms in facilities that have no other means of obtaining biofilm samples such as in pipelines without corrosion coupons or in pipelines with low water cut. The primary pressurized chamber 116 may act as a separator that allows for produced water to drop out and hence for initiation of biofilm growth and potentially microbiologically influenced corrosion on the one or more coupons.

Aspects of the disclosure may include any combinations of the methods and systems shown in the following numbered paragraphs. This is not to be considered a complete listing of all possible aspects, as any number of variations can be envisioned from the description above.

1. A method for testing properties of a pressurized multiphase fluid sample containing at least hydrocarbons and water, the method comprising:
   placing the pressurized multiphase fluid sample into a first pressurized chamber of a testing device;
   separating the water from the hydrocarbons;
   through a first outlet in the first pressurized chamber, flowing at least part of the separated water into a second pressurized chamber;
   optionally isolating the second pressurized chamber from the first pressurized chamber;
   testing a pH level of the separated water in the second pressurized chamber; and
   in the first pressurized chamber, testing for microbial activity and growth in the pressurized multiphase fluid;
   while substantially maintaining a pressure of the pressurized multiphase fluid throughout the placing, separating, flowing, isolating, and testing steps.

2. The method of paragraph 1, further comprising:
   disposing of the liquid hydrocarbons through a second outlet in the first pressurized chamber.

3. The method of paragraph 1 or paragraph 2, further comprising:
   providing for visual inspection of an interior of the first pressurized chamber.

4. The method of paragraph 3, wherein the visual inspection is provided for using at least one inspection port.

5. The method of any of paragraphs 1-4, wherein testing for microbial activity and growth in the hydrocarbons comprises:
   placing a corrosion coupon in the first pressurized chamber;
   while substantially maintaining the pressure of the pressurized multiphase fluid in the first pressurized chamber, maintaining the corrosion coupon in the first pressurized chamber for sufficient time to permit microbial activity and/or growth on the corrosion coupon; and
   removing the corrosion coupon from the first pressurized chamber.

6. The method of paragraph 5, further comprising:
   draining the separated water from the first pressurized chamber to ensure hydrocarbons contact the corrosion coupons.

7. The method of paragraph 5, further comprising:
   periodically replacing the pressurized multiphase fluid sample while maintaining the corrosion coupon in the first pressurized chamber, to provide nutrients for the microbial activity and/or growth on the corrosion coupon.

8. The method of any of paragraphs 1-7, wherein the isolating step is accomplished using an actuatable valve.

9. The method of any of paragraphs 1-8, wherein the pressurized multiphase fluid is a hydrocarbon production fluid, and further comprising obtaining the hydrocarbon production fluid from a pipeline.

10. An apparatus for testing properties of a pressurized multiphase fluid sample containing at least hydrocarbons and water, the apparatus comprising:
    a first pressurized chamber into which the pressurized multiphase fluid sample and one or more corrosion coupons are placed;
    a second pressurized chamber connected to the first pressurized chamber through a first outlet;
    a first valve disposed between the first pressurized chamber and the second pressurized chamber, the first valve configured to open to permit water separated out of the pressurized multiphase fluid sample in the first pressurized chamber to flow into the second pressurized chamber, the first valve configured to close to prevent hydrocarbons in the pressurized multiphase fluid sample from flowing into the second pressurized chamber from the first pressurized chamber;
    a pH probe positioned to test a pH level of the separated water in the second pressurized chamber; and
    a viewing port disposed in the first pressurized chamber to permit visual inspection of at least one of the pressurized multiphase fluid sample and the one or more corrosion coupons in the first pressurized chamber.

11. The apparatus of paragraph 10, wherein the pressurized multiphase fluid sample is taken from one of a production flow, a pipeline flow, a separator, a storage tank, and a vessel.

12. The apparatus of paragraph 10 or paragraph 11, further comprising a second valve positioned at an outlet of the second pressurized chamber, the second valve configured to close to maintain the separated water in the second pressurized chamber while the pH level of the separated water is being tested, the second valve configured to open to permit the separated water to exit the second pressurized vessel.

13. The apparatus of any of paragraphs 10-12, further comprising:
    a coupon holder configured to hold a corrosion coupon in place such that fluid in the primary pressurized chamber contacts the corrosion coupon.

14. A method for testing properties of a pressurized multiphase fluid sample containing at least hydrocarbons and water, the method comprising:
    placing the pressurized multiphase fluid sample into a first pressurized chamber of a testing device;
    separating the water from the hydrocarbons;
    through a first outlet in the first pressurized chamber, flowing at least part of the separated water into a second pressurized chamber;
    optionally isolating the second pressurized chamber from the first pressurized chamber; and
    testing a pH level of the separated water in the second pressurized chamber;
    while substantially maintaining a pressure of the pressurized multiphase fluid throughout the placing, separating, flowing, isolating, and testing steps.

15. The method of paragraph 14, further comprising:
    disposing of the liquid hydrocarbons through a second outlet in the first pressurized chamber.

16. The method of paragraph 14 or paragraph 15, further comprising:
    providing for visual inspection of an interior of the first pressurized chamber.

17. The method of paragraph 16, wherein the visual inspection is provided for using at least one inspection port.

While the foregoing is directed to aspects of the present disclosure, other and further aspects of the disclosure may be devised without departing from the basic scope thereof, and the scope thereof is determined by the claims that follow.

What is claimed is:

1. A method for testing properties of a pressurized multiphase fluid sample containing at least hydrocarbons and water, the method comprising:
   placing the pressurized multiphase fluid sample into a first pressurized chamber of a testing device wherein the first pressurized chamber comprises at least one viewing port which provides for visual inspection of an interior of the first pressurized chamber;
   separating the water from the hydrocarbons;
   through a first outlet in the first pressurized chamber, flowing at least part of the separated water into a second pressurized chamber;
   optionally isolating the second pressurized chamber from the first pressurized chamber;
   testing a pH level of the separated water in the second pressurized chamber; and
   in the first pressurized chamber, testing for microbial activity and growth in the pressurized multiphase fluid;
   while substantially maintaining a pressure of the pressurized multiphase fluid throughout the placing, separating, flowing, isolating, and testing steps.

2. The method of claim 1, further comprising:
   disposing of the hydrocarbons through a second outlet in the first pressurized chamber.

3. The method of claim 1, wherein testing for microbial activity and growth in the hydrocarbons comprises:
   placing a corrosion coupon in the first pressurized chamber;
   while substantially maintaining the pressure of the pressurized multiphase fluid in the first pressurized chamber, maintaining the corrosion coupon in the first pressurized chamber for sufficient time to permit microbial activity and/or growth on the corrosion coupon; and
   removing the corrosion coupon from the first pressurized chamber.

4. The method of claim 3, further comprising:
   draining the separated water from the first pressurized chamber to ensure hydrocarbons contact the corrosion coupons.

5. The method of claim 3, further comprising:
   periodically replacing the pressurized multiphase fluid sample while maintaining the corrosion coupon in the first pressurized chamber, to provide nutrients for the microbial activity and/or growth on the corrosion coupon.

6. The method of claim 1, wherein the steps include the isolating the second pressurized chamber from the first pressurized chamber and the isolating is accomplished using an actuatable valve.

7. The method of claim 1, wherein the pressurized multiphase fluid is a hydrocarbon production fluid, and further comprising obtaining the hydrocarbon production fluid from a pipeline.

8. An apparatus for testing properties of a pressurized multiphase fluid sample containing at least hydrocarbons and water, the apparatus comprising:
   a first pressurized chamber into which the pressurized multiphase fluid sample and one or more corrosion coupons are placed;
   a second pressurized chamber connected to the first pressurized chamber through a first outlet;
   a first valve disposed between the first pressurized chamber and the second pressurized chamber, the first valve configured to open to permit water separated out of the pressurized multiphase fluid sample in the first pressurized chamber to flow into the second pressurized chamber, the first valve configured to close to prevent hydrocarbons in the pressurized multiphase fluid sample from flowing into the second pressurized chamber from the first pressurized chamber;
   a pH probe positioned to test a pH level of the separated water in the second pressurized chamber; and
   a viewing port disposed in the first pressurized chamber to permit visual inspection of at least one of the pressurized multiphase fluid sample and the one or more corrosion coupons in the first pressurized chamber.

9. The apparatus of claim 8, wherein the pressurized multiphase fluid sample is taken from one of a production flow, a pipeline flow, a separator, a storage tank, and a vessel.

10. The apparatus of claim 8, further comprising a second valve positioned at an outlet of the second pressurized chamber, the second valve configured to close to maintain the separated water in the second pressurized chamber while the pH level of the separated water is being tested, the second valve configured to open to permit the separated water to exit the second pressurized vessel.

11. The apparatus of claim 8, further comprising:
    a coupon holder configured to hold a corrosion coupon in place such that fluid in the primary pressurized chamber contacts the corrosion coupon.

12. A method for testing properties of a pressurized multiphase fluid sample containing at least hydrocarbons and water, the method comprising:
    placing the pressurized multiphase fluid sample into a first pressurized chamber of a testing device wherein the first pressurized chamber comprises at least one viewing port which provides for visual inspection of an interior of the first pressurized chamber;
    separating the water from the hydrocarbons;
    through a first outlet in the first pressurized chamber, flowing at least part of the separated water into a second pressurized chamber;
    optionally isolating the second pressurized chamber from the first pressurized chamber; and
    testing a pH level of the separated water in the second pressurized chamber;
    while substantially maintaining a pressure of the pressurized multiphase fluid throughout the placing, separating, flowing, isolating, and testing steps.

13. The method of claim 12, further comprising:
    disposing of the hydrocarbons through a second outlet in the first pressurized chamber.

* * * * *